(12) United States Patent
Elstroem (10) Patent No.: US 9,587,866 B2
(45) Date of Patent: Mar. 7, 2017

(54) SYSTEM OR METHOD FOR MEASURING THE PHASE OF AMMONIA IN A COOLING SYSTEM

(75) Inventor: Michael Elstroem, Noerre Snede (DK)

(73) Assignee: HP Products A/S, Hasselager (DK)

(*) Notice: Subject to any disclaimer, the term of this patent is extended or adjusted under 35 U.S.C. 154(b) by 679 days.

(21) Appl. No.: 13/884,620

(22) PCT Filed: Nov. 11, 2011

(86) PCT No.: PCT/DK2011/050427
§ 371 (c)(1),
(2), (4) Date: Jul. 19, 2013

(87) PCT Pub. No.: WO2012/062329
PCT Pub. Date: May 18, 2012

(65) Prior Publication Data
US 2013/0291568 A1    Nov. 7, 2013

(30) Foreign Application Priority Data
Nov. 12, 2010   (DK) .................... 2010 70486

(51) Int. Cl.
*F25B 49/02*       (2006.01)
*F25B 41/06*       (2006.01)
(Continued)

(52) U.S. Cl.
CPC ............ *F25B 49/02* (2013.01); *F25B 41/062* (2013.01); *G01F 23/04* (2013.01); *G01F 23/268* (2013.01);
(Continued)

(58) Field of Classification Search
CPC .... F25B 41/062; F25B 49/02; F25B 2500/28; F25B 2700/00; G01F 23/04; G01F 23/268; G01N 27/22
See application file for complete search history.

(56) References Cited

U.S. PATENT DOCUMENTS

| 3,321,726 A | 5/1967 | Babylon |
| 4,344,293 A | 8/1982 | Fujiwara et al. |

(Continued)

FOREIGN PATENT DOCUMENTS

| EP | 2 088 405 A2 | 8/2009 |
| JP | 55-158551 A | 12/1980 |

(Continued)

OTHER PUBLICATIONS

Danish Patent and Trademark Office Search Report Dated Jun. 27, 2011 of Application No. PA 2010 70486.

(Continued)

*Primary Examiner* — Marc Norman
(74) *Attorney, Agent, or Firm* — David S. Safran (57) ABSTRACT

A system or a method for performing capacitive sensing of humidity/liquid, primarily in conductive or non-conductive liquid/gas mixtures, having a control unit and at least first and second sensor electrodes, the capacity between the first and the second electrodes being measured. To measure humidity/liquid in a circulating gas/liquid mixture at least one of the sensor electrodes is formed as a tube which is placed in the liquid/gas mixture. Based on the capacitive measurements, a calculation of at least one dataset for control of a second system is performed. The tube can be more or less filled up with liquid or gas and the capacity can be measured as it depends on the content around or inside the tube, and if a dry gas is there will be one value of capacity and in a situation where the gas is being replaced by liquid, the capacity value will change rapidly.

5 Claims, 5 Drawing Sheets (51) Int. Cl.
*G01N 27/22* (2006.01)
*G01F 23/04* (2006.01)
*G01F 23/26* (2006.01)

(52) U.S. Cl.
CPC .......... *G01N 27/22* (2013.01); *F25B 2500/28* (2013.01); *F25B 2700/00* (2013.01)

(56) References Cited

U.S. PATENT DOCUMENTS

| | | | | |
|---|---|---|---|---|
| 5,214,918 | A | * | 6/1993 | Oguni et al. ........................ 62/56 |
| 5,353,604 | A | * | 10/1994 | Oguni et al. ..................... 62/207 |
| 5,410,887 | A | | 5/1995 | Urata et al. |
| 6,568,195 | B2 | * | 5/2003 | Kaimai .................. C09K 5/041 252/68 |
| 6,634,182 | B2 | * | 10/2003 | Ichikawa ................ F25B 9/002 165/164 |
| 6,708,520 | B2 | * | 3/2004 | Yasunori ............... F04C 23/008 62/114 |
| 6,966,196 | B2 | * | 11/2005 | Matsuki ................ F25B 49/005 62/228.1 |
| 8,146,421 | B2 | | 4/2012 | Jacobson et al. |
| 2011/0214438 | A1 | | 9/2011 | Larsen et al. |

FOREIGN PATENT DOCUMENTS

| | | |
|---|---|---|
| JP | 59-229155 A | 12/1984 |
| JP | 07-146042 A | 6/1995 |
| JP | 09-96618 A | 4/1997 |
| SU | 1618876 A1 | 1/1991 |
| SU | 1711057 A1 | 2/1992 |
| WO | 2010/025730 A1 | 3/2010 |
| WO | 2010/077893 A1 | 7/2010 |

OTHER PUBLICATIONS

International Search Report of International Application No. PCT/DK2011/050427 Date of Mailing of the International Search Report Jan. 16, 2012.

* cited by examiner

SYSTEM OR METHOD FOR MEASURING THE PHASE OF AMMONIA IN A COOLING SYSTEM

BACKGROUND OF THE INVENTION

Field of the Invention

A refrigeration system comprising at least one compressor, which compressor delivers compressed refrigerant gas to at least one condenser, which condenser delivers liquid refrigerant to at least one flow restriction, from which flow restriction low pressure refrigerant flows to at least one evaporator, from which evaporated refrigerant flows back to the compressor, which system comprises at least one sensor for detecting liquid in the suction gas which sensor is connected to a control unit, which control unit performs control of the refrigeration system, which sensor is formed as at least one capacitive sensor, which capacitive sensor comprises at least a first and a second sensor electrode, which capacity censor at least measures the capacity between at least the first and at least the second electrode, at least one of the sensor electrodes are formed as a tube Description of Related Art International Patent Application Publication WO 2010/025730 A1 and corresponding U.S. Patent Application Publication 2011/0214438 disclose a method for controlling a flow of refrigerant to an evaporator arranged in a refrigeration system. The refrigeration system further comprises an expansion valve and a compressor, the expansion valve, the evaporator and the compressor being arranged in a refrigerant flow path having refrigerant flowing therein. The method comprises the steps of increasing an opening degree of the expansion valve, thereby increasing a flow of refrigerant to the evaporator sufficiently to substantially eliminate a dry zone of the evaporator, decreasing the opening degree of the expansion valve after a period of time has lapsed, and repeating the steps of increasing and decreasing the opening degree of the expansion valve. Thus, the opening degree of the expansion valve is 'pulsated'. This causes the superheat value of refrigerant leaving the evaporator to 'toggle' between a zero level and a low, but positive, level. Thereby the average superheat value of the refrigerant leaving the evaporator is decreased, and the refrigeration capacity of the evaporator is utilised more efficiently. Simultaneously, it is ensured that the amount of liquid refrigerant being allowed to pass through the evaporator is kept sufficiently low to prevent damage to the compressor.

European Patent Application EP 2 088 405 A2 and corresponding U.S. Pat. No. 8,146,421 concern a method and apparatus for sensing levels of insoluble fluids within a storage vessel utilizing an array of main capacitive sensors having differing geometries. The array of main capacitive sensors gives the ability to measure the levels of insoluble liquids in a vessel. Each of the main capacitive sensors include at least one pair of conductive plates capable of submersion in the at least two insoluble fluids, and the geometries of the pair of conductive plates differ and are distinct, such as in distance or in width, in each of the main capacitive sensors. In addition, the apparatus and method may include at least one reference sensor placed intermittently along the height of the vessel to provide input as to the permittivities of the insoluble fluids.

Japanese Patent Application Publication JP 09 09 6618 A concerns an apparatus with sufficient accuracy for detecting state of a refrigerant, by outputting continuous electric signals proportional to the ratio of gas state and liquid state. Whereby the refrigerant state-detecting apparatus for detecting the state of a refrigerant in a circulation path. A state detection means and a detection circuit are provided in the circulation path. The state detection means has at least two sheets of flat electrodes held via a small gap to the parallel to a flow of the refrigerant, and the detection circuit takes out the change of capacitance of the state detection means in accordance with the change of dielectric constant of the refrigerant liquid as the change of voltage.

SUMMARY OF THE INVENTION

The object of the invention is to measure phase of refrigerant (saturated/superheated).

The object can be fulfilled by a system as initially described above if further modified so the tubes are measuring the liquid/gas phase of the suction gas between evaporator and compressor, which control system is based on the capacitive measurements where the system performs a calculation of at least one dataset for control of the refrigeration system.

Hereby can be achieved that the tube can be more or less filled up with liquid or gas and the capacity can be measured, which capacity will depend on the content around or inside the tube, because if it is a dry gas there will be one value of capacity and in a situation where the gas is becoming filled with liquid, the capacity value will change rapidly. The capacity will change the more wet the liquid the gas will be, ending up with total submersion of the tube. In a submerged situation the capacity value can be indicated, but this value is most different form the value, when it is dry gas that is in the tube. Thereby, not only situations can be measured, but even slight change in the content of the gas can be indicated. Based on the measurement, further control values can be generated for controlling a system where gas or liquid are circulating. That could be important for example in cooling systems.

The first and second censor electrodes can be formed mostly coaxial, forming a first outer electrode tube, which first outer electrode tube contains the second inner electrode tube. By coaxial tubes it is possible to measure the capacity between the tubes. Liquid or gas can flow between and inside the tubes, so an effective indication of humidity can be achieved.

The first outer sensor can be part of a tube in a cooling system, which second inner tube is placed inside the outer tube and electric isolated from the outer tube, which system measures the capacity between the first outer tube and the second inner tube. Especially in cooling systems it is important to indicate for example overheating in an evaporator. In different places in a cooling system it can be very important to measure the gas and get an effective indication of the content of liquid drops in the gas. Especially the suction line towards a compressor is rather important to secure compressors against liquid hammer.

The outer tube can be part of a tube connecting an evaporator with s suction inlet to a compressor for indicating liquid in the suction gas. The indication of liquid in a suction line is not only important in relation to protecting the compressor, but also in relation to achieving the most effective use of an evaporator.

The system can be used for control of an expansion valve, which expansion valve controls liquid inlet to the evaporator and thereby control of the overheating of the evaporator. A very effective control of an expansion valve could be achieved by measuring the gas leaving the evaporator. In that way it should be possible to reduce the overheating of the evaporator and thereby achieve a much more effective evaporator. In traditional control of expansion valves, temperature of the gas leaving the evaporator or the pressure of the gas has been used for controlling the expansion valves. Also an electronic control system has been used for controlling the expansion valve. In all situations there is no effective protection against liquids in the gas leaving the evaporator, if not a certain overheating is allowed. Therefore, it is possible to indicate humidity in the gas leaving the evaporator. Thereby it is possible to shut down the expansion valve shortly, until the gas leaving the evaporator is dry. In that way a much more effective use of an evaporator is possible.

The system can be used for control of a compressor, which control system is used as a liquid alarm, which liquid alarm stops the compressor if liquid particles are indicated in the suction gas. By measuring liquid particles in the suction gas directly before the inlet at the suction tube at a compressor, it is possible to prevent liquid particles entering the compressor. If the compressor is connected to the control system, it is possible in some situations to shut off the compressor. In other situations, if the compressor is operating with variable speed, it is possible to reduce the speed of the compressor and in that way allow liquid particles in the gas to evaporate. A safety circuit for a compressor can be rather important, even in situations where the system has never come to an actual use. The existence of the safety system can lead to a situation where a gas at a lower temperature can be used as suction gas, and in that way increase the effectivity of the compressor. It is by the safety system possible to operate with very limited superheating of the gas.

This invention further concerns a method for indicating liquid ammonia in a cooling system, where at least a first measuring electrode is placed inside a cooling circuit, where the electrode are connect to a measuring circuit, where measurement of the capacity between electrode and a reference is performed, where the measured capacity is transmitted to a control system, where control of the cooling system based on the measured capacity is performed, where the capacity is measure between an inner tube and an outer tube, where measurement of liquid particles in ammonia gas flowing in the outer and inner tube towards a compressor is performed.

By the method as described there can be achieved a highly effective measuring system, for example for ammonia or carbon dioxide cooling circuits. The method could in that way concern the control of a suction gas, but also level indicators.

DETAILED DESCRIPTION OF THE INVENTION

Figure 1:
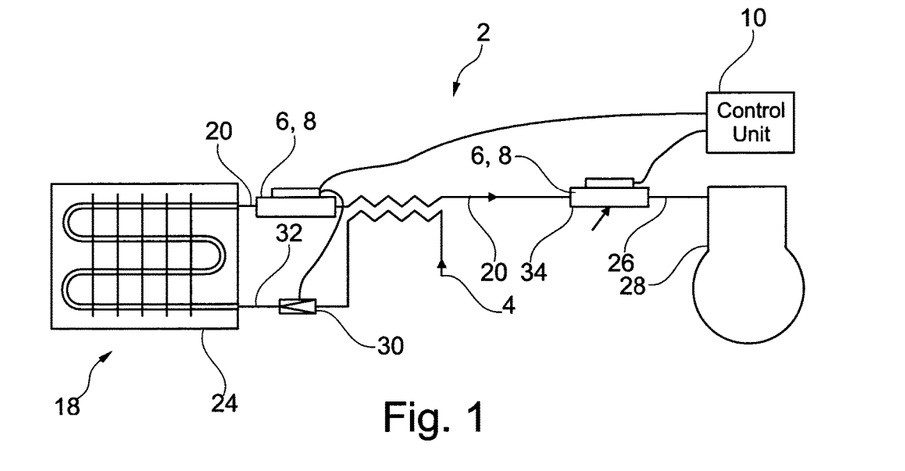
FIG. 1 shows a schematic view of a cooling system, where

FIG. 1 shows a cooling system 2 which cooling system comprises a cooling media for circulating in the system. Sensors 6.8 are placed in the gas return line 20 which is leading from an evaporator 24 through the first sensor 6.8 towards the second sensor 6.8 further through the suction line 26 to the compressor 28. The two sensors 6.8 are both connected to the control unit 10. From the compressor 28, the compressed refrigerant is sent to a not shown condenser where liquid refrigerant 4 is received and sent to the expansion valve 30. From the expansion valve 30 leads a tube 32 into the evaporator 24.

In operation the first of the sensors 6.8 can measure the content of humidity in the gas in the line 20 leaving the evaporator. This measurement can be used for controlling the expansion valve. As long as the gas leaving the tube 20 is dry, the expansion valve can remain open. As soon as liquid is indicated in the line 20, the expansion valve can be reduced in its opening, so further evaporation takes place. Hereby it is possible to operate the evaporator with a very limited superheating. Furthermore, before the gas enters the compressor further one detector 6.8 is indicated as 34. This sensor 6.8 and 34 is used as a liquid alarm. If liquid is detected, the compressor might be shut down or the speed is reduced.

Figure 2:
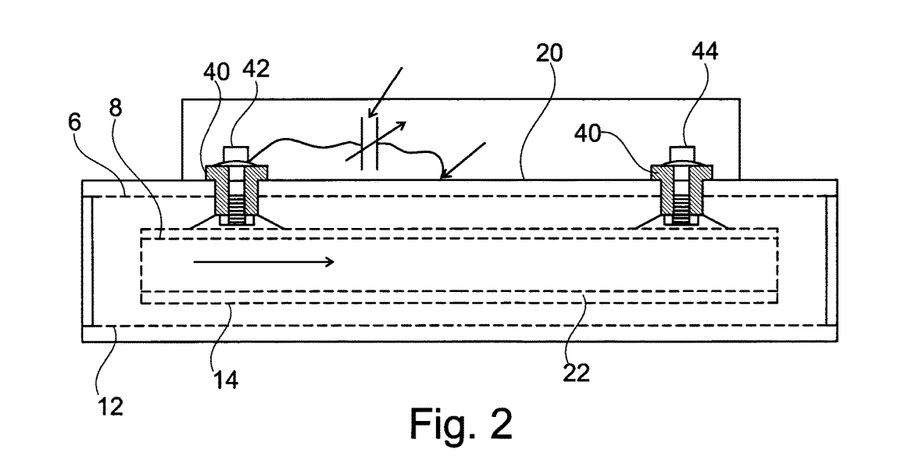
FIG. 2 shows a section of a suction tube.

FIG. 2 shows a sectional view of a tube section, for example the tube 20 at the FIG. 1. The detector is made inside the tube 20 where the detector 6 and 12 are all referring to the same component. Inside the tube 20 is indicated an inner tube which is indicated as 8, 14 and 22. The inner tube 22 is kept in place by fixtures 40 where a conducting screw 42 connects the inner tube 22 electrically and where the screw 44 is an isolating screw that isolated the inner tube towards the outer tube 20. In operation it is possible to measure the capacity between the inner tube and the outer tube. Since the flow of liquid or gas is passing through both the tubes, there is nearly no flow restriction. However, even small amounts of liquid in the circulating gas can be detected, because even small drops of liquid have a relatively high influence on the capacity that is measured between the two tubes. Therefore it is possible by the capacity measurement to indicate liquid particles in gas, and therefore adjustment of a cooling system can be performed immediately.

Figure 3:
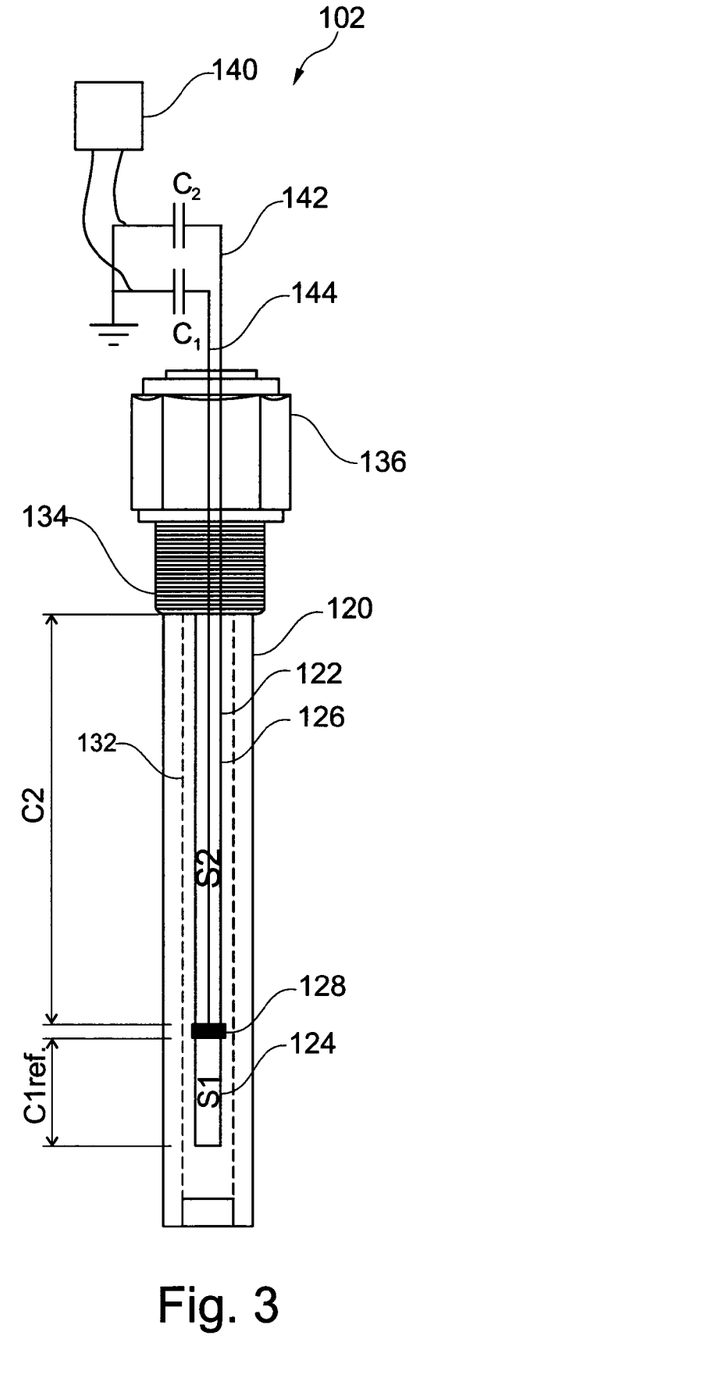
FIG. 3 shows a level indicator,
FIG. 4 show a second section of a suction tube.

FIG. 3 shows a system 102 for level detection. The level detector comprises an outer tube 120 and an inner tube 122. The inner tube comprises a first section 124 and the second section 126. The two sections are separated by isolation means 128. The inner tube 122 is placed inside a partly open tube 132. The inner tube and the outer tube are placed in relation to a screw 134 and a housing 134. A measuring system 140 is connected to the lines 142, 144. The line 142 is connected to the tube section 126 and the second line 144 is connected to the tube section 124.

In operation, a reference can be achieved if the section 124 is submerged in the liquid. Thereby a reference value can be calculated. The tube section 126 can hereafter perform an indication of the level of liquid around the tube. In that way it is possible to indicate the level of, for example, refrigerant in one or another tank as part of a refrigeration system, or it is possible to indicate the level of oil in a refrigeration system. The system at FIG. 3 can be a highly effective oil indicator in refrigeration systems. The system could be placed, for example, in a submerged evaporator and there it could indicate the oil level in the evaporator. Hereby it is possible to start a pump or indicate that manual opening of a valve to tap the oil is necessary. In many modern systems the oil return is performed automatically by pumping systems.

Figure 4:
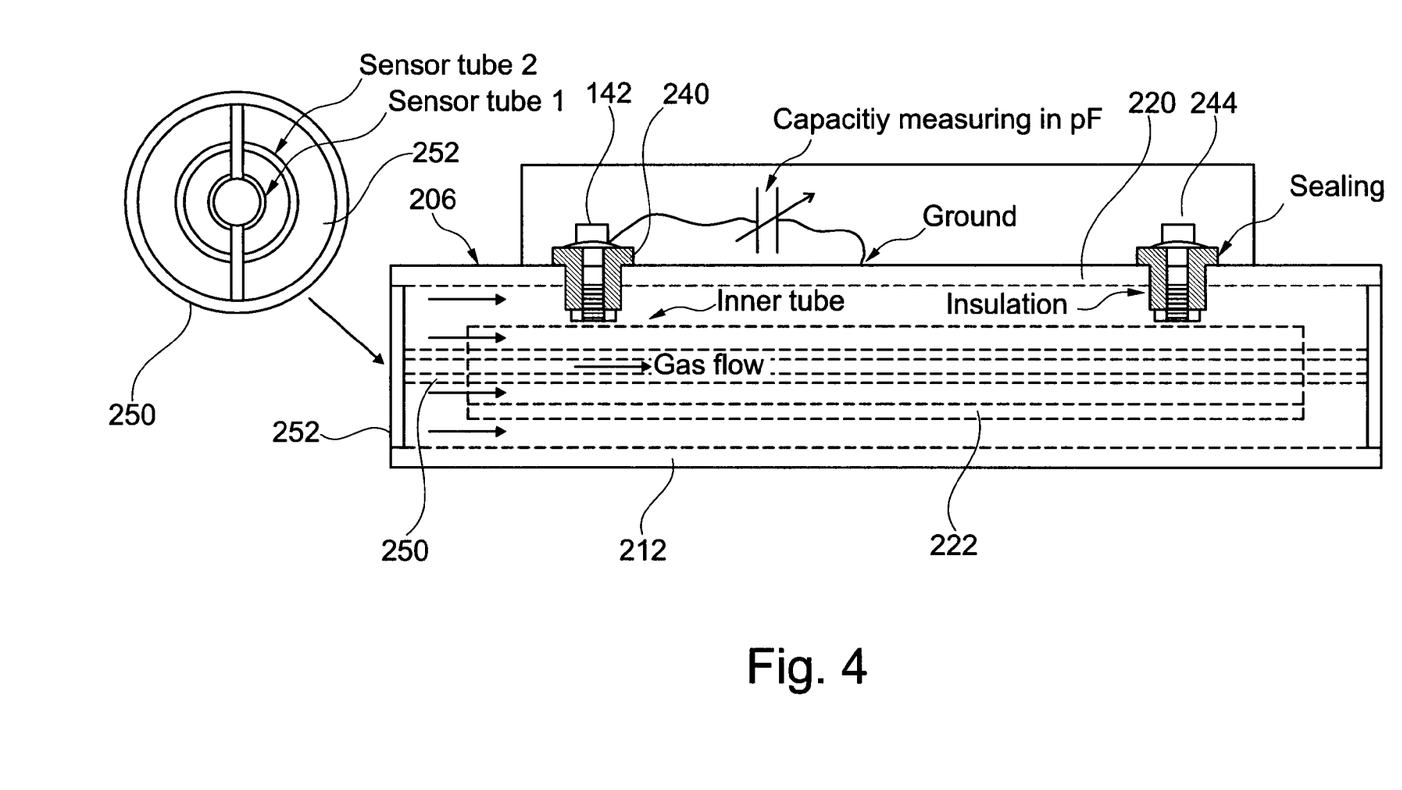

FIG. 4 shows a sectional view of a tube section, for example the tube 220 at the FIG. 4. The detector 206 is made inside the tube 220 where the detector 206 and 212 are all referring to the same component. Inside the tube 220 is indicated an inner tube 222. The inner tube 222 is kept in place by fixtures 240 where a conducting screw 242 connects the inner tube 222 electrically and where the screw 244 is an isolating screw that isolated the inner tube towards the outer tube 220. The detector 206 further comprises a second inner tube 250, which second inner tube 250 is fixed to the outer tube 220 by conductive fixtures 252.

In operation, it is possible to measure the capacity between the inner tube and the outer tube and also between the first inner tube and the second inner tube. Hereby is the actual electric capacity increased and more accurate measurement can be achieved.

FIGS. 5a-5d shows a cooling system which is divided into four different subsystems where only a compressor 328, a condenser 340, and a receiver 342 are common.

Figures 5, 5A, 5B, 5C, 5D:
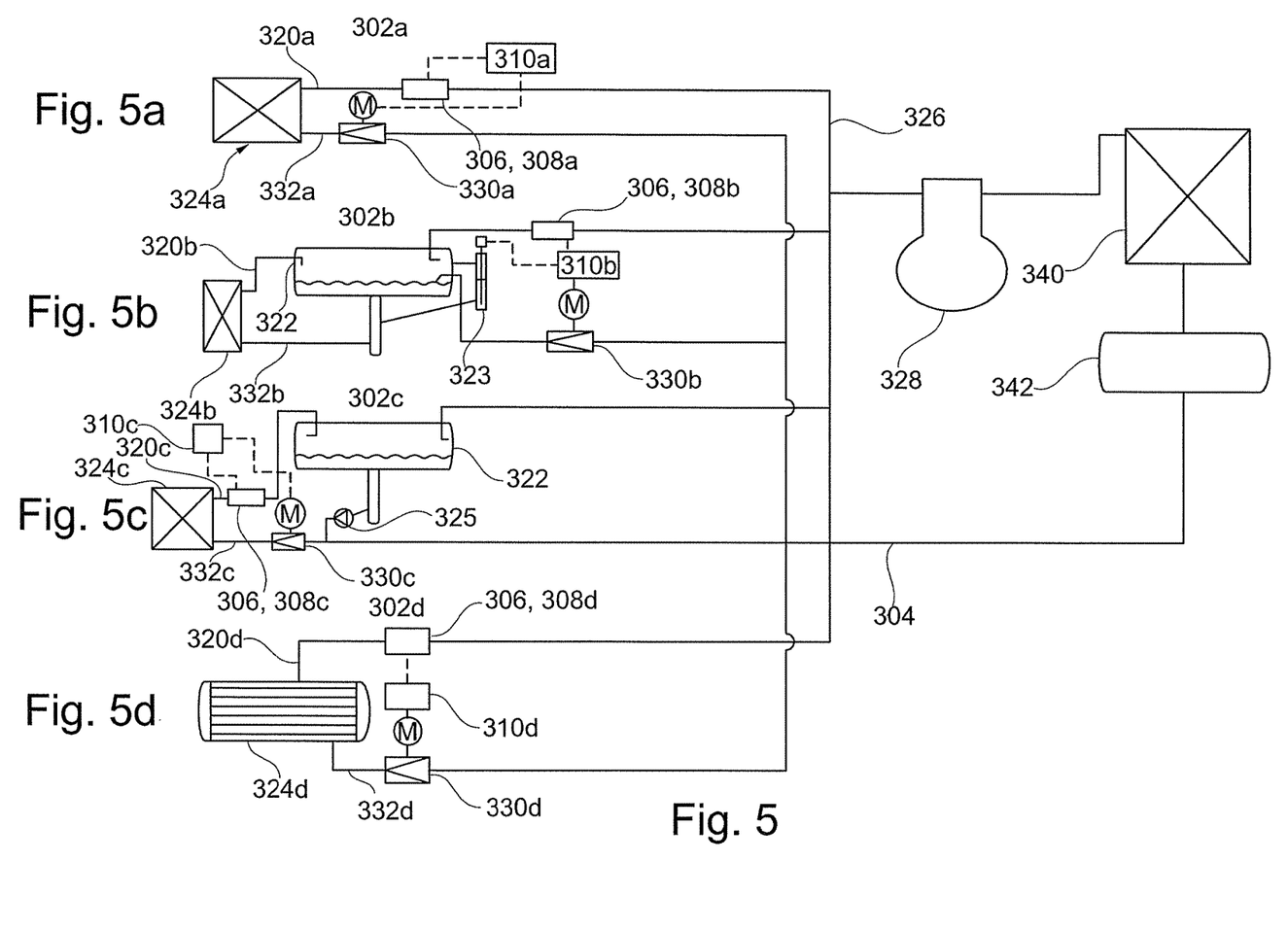
FIGS. 5a-5d show four possible embodiments for cooling systems, and
FIG. 6 show the relation between density of refrigerant and the sensor level.

FIG. 5a shows a system 302a which is by a high pressure line 304 connected to the receiver 342. This line 304 is connected to an expansion valve 330a and further through a connection line 332a to an evaporator 324a. A suction line 320a is connected to a sensor 306,308a which is electrically connected to a control unit 310a. A suction line 326 is connects the refrigerant to the suction side of a compressor 328.

In operation, the sensor 306,308a will measure the suction gas and indicate any liquid drops that are carried in the gas. The control unit 31a controls the expansion valve 330a so by indicating any liquid drop in the sensor 306,308, the expansion valve is more or less closed, or at least the flow though the expansion valve 330a is reduced. In this way it is achieved that the suction gas that reaches the compressor 328 is absolutely dry and free from any liquid droplets.

In FIG. 5b the expansion valve 330b is also connected to the line 304 from the receiver 342. The expansion valve 330b is delivering liquid refrigerant to a tank 322 from where a line 332b is connected to the evaporator 324b. The evaporator is connected by a line 320b into the tank 322. From the tank 322 there is a suction line connected to the sensor 306,308b. The sensor 306,308b is connected to a control unit 310b which is further connected to a liquid level indicator 323. The control unit 310b is controlling the flow through the expansion valve 330b so that the liquid level in the tank 322 can be controlled. In this way the liquid level can be under control according to two different parameters. One parameter is the liquid level, the other is the existence of liquid drops in the detector 306,308b. In this way it can be achieved that the will always be sufficient liquid refrigerant for the evaporator 324b, and there will always be control of the suction gas delivered to the compressor. The use of the tank 322 has the advantage that the evaporator 324 can be fully submerged. The tank 322 operates as a liquid separator.

FIG. 5c shows a subsystem 302c. Again the line 304 is connected to the expansion valve 330c from which expansion valve 330c a line 332c connects towards the evaporator 324c. The outlet of the evaporator 324c is via a line 320c connected to a sensor 306,308c. The outlet of this sensor is connected to a separation tank 322. From this separation tank evaporated refrigerant is sucked to the suction side of the compressor 328. Liquid refrigerant is collected by a pump 325 which pump outlet is connected to the pressure line 304 that supplies liquid refrigerant towards the expansion valve 330c. By means of the control unit 310c the sensor 306,308c controls the expansion valve 330c and the pump 325.

Hereby a total control of the evaporator 324c can be achieved. At the same time it is achieved that no liquid droplets will be contained in the suction gas that reaches the compressor 328.

FIG. 5d shows a system 302d which, like the ones previously described, also receives liquid high-pressure refrigerant over the line 304. The expansion valve 330d is further connected by a line 332d to a submerged evaporator 324d. A line 320d is connecting sensor 306,308d to the suction line 326 connected to the suction side of the compressor 328. The sensor 306,308d is connected to a control unit 310d which controls the expansion valve 330d. In this way it is possible to close or reduce the flow through the expansion valve when droplets of liquid refrigerant are measured by the sensor 306,308d. In this way it can be ensured that the suction line towards the compressor only carries dry gas and the evaporator is completely filled with liquid refrigerant.

A system as shown in FIG. 5 could be used for different types of refrigerant where one possible refrigerant can be ammonia NH3.

Figure 6:
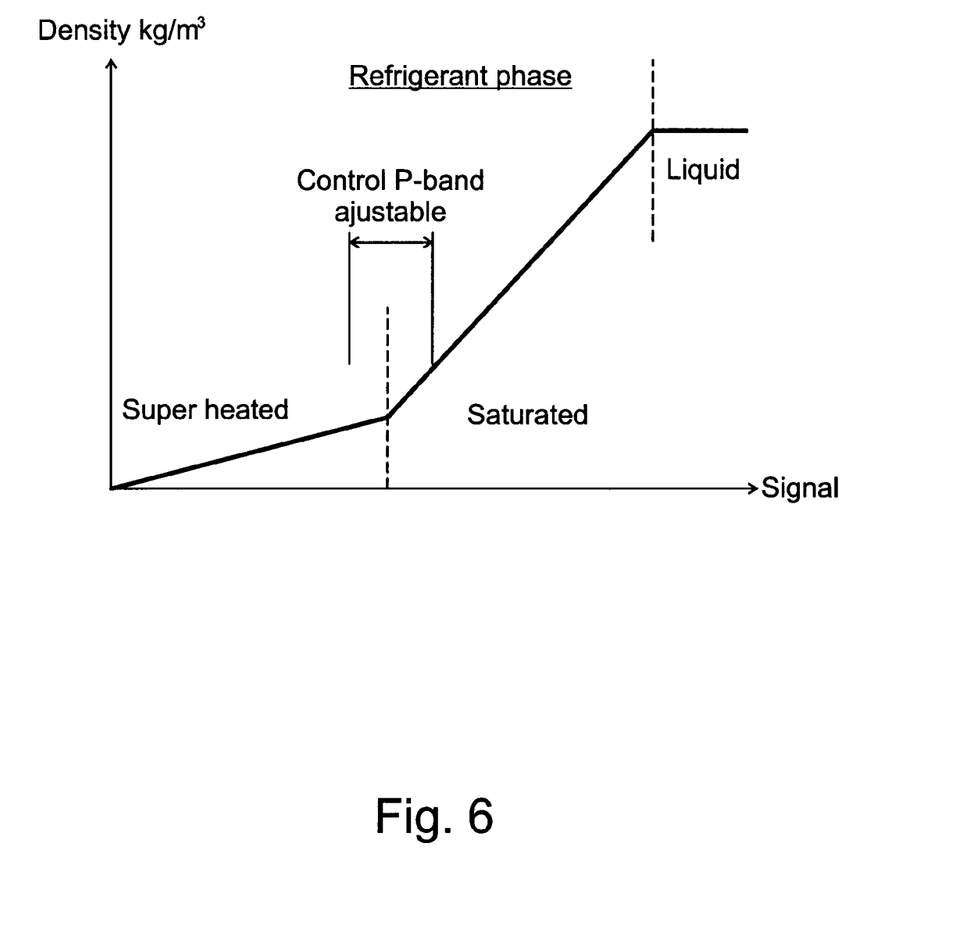

FIG. 6 shows a coordinate system which vertical axes indicate the density of the refrigerant flowing through a sensor, and the horizontal axis shows the signal level that can be indicated. The curve that is shown indicates that a relatively low signal level is achieved if superheated refrigerant is passing the sensor. But, as the refrigerant starts to be saturated there is a rapid increase in the signal level. That increase in signal level continues until the refrigerant phase becomes totally liquid. Indicated at FIG. 6 is the control P-band where the refrigeration system mostly is operating where there is the area around the superheated and the saturated phase.

Operating in the said P-band, it is possible to avoid liquid refrigerant in the suction line towards the compressor and in that way totally avoid compressor hamming. A further effect that is achieved is that the cooling system can operate very near the saturated system whereby the effectivity of evaporators is increasing.

It is also possible to use the capacitive sensors to control humidity content in intake air for combustions processes. By using the humidity content as input for a computer system that controls the combustion process it is possible to reduce pollution and reduce fuel consumption. The system can be used for control of engines in ships, cars or aeroplanes.

What is claimed is:

1. A refrigeration system for ammonia comprising at least one compressor which delivers compressed ammonia gas to at least one condenser, which condenser delivers liquid ammonia to at least one flow restriction, from which flow restriction, low pressure ammonia flows to at least one evaporator having a liquid ammonia inlet, from which evaporated ammonia flows back to the compressor, an expansion valve which controls the liquid ammonia inlet, which system comprises at least one sensor for detecting liquid ammonia in suction gas, the sensor being formed as at least one capacitive sensor that is connected to a control unit, which control unit controls operation of the refrigeration system, which capacitance sensor comprises at least a first and a second sensor electrode, which capacitance sensor at least measures the capacitance between at least the first and at least the second electrodes, where at least one of the sensor electrodes is formed as a tube which measures the liquid/gas content of the suction ammonia gas flowing from the evaporator towards the compressor, which control system, based on measurements obtained by the at least one capacitive sensor, is adapted to calculate at least one dataset for controlling the refrigeration system, whereby the system is adapted for controlling an expansion valve so as to reduce overheating of the evaporator based on the liquid/gas content of the suction ammonia gas measured.

2. A refrigeration system according to claim 1, whereby the first and second sensor electrodes are essentially coaxial, forming a first outer electrode tube and at least one second inner electrode tube.

3. A refrigeration system according to claim 2, whereby the first outer sensor is part of a tube in a cooling system, which at least one second inner tube is placed inside the outer tube in a manner electrically isolated from the outer tube, which system measures the capacitance between the first outer tube and at least one second inner tube.

4. A refrigeration system according to claim 3, whereby the outer tube is part of a tube connecting an evaporator with the suction inlet of the compressor for indicating liquid ammonia in the suction gas.

5. Method for indicating liquid ammonia in a cooling system, which method comprises at least the following steps:
  a. placing at least a first measuring electrode inside a cooling circuit,
  b. connecting the electrode to a measuring circuit,
  c. performing measurement of the capacitance between the electrode and a reference,
  d. transmitting the measured capacitance to a control system,
  e. performing control of the cooling system based on the measured capacity,
  f. measuring the capacitance between an inner tube and an outer tube,
  g. performing measurement of liquid in ammonia gas flowing in the outer and inner tube towards a compressor based on the capacitance measured,
  h. performing control of the cooling system based on the measurement of liquid ammonia in the suction gas.

* * * * *

UNITED STATES PATENT AND TRADEMARK OFFICE
CERTIFICATE OF CORRECTION

| | | |
|---|---|---|
| PATENT NO. | : 9,587,866 B2 | Page 1 of 1 |
| APPLICATION NO. | : 13/884620 | |
| DATED | : March 7, 2017 | |
| INVENTOR(S) | : Michael Elstroem | |

It is certified that error appears in the above-identified patent and that said Letters Patent is hereby corrected as shown below:

On the Title Page

(75) Inventor should read as: Michael Elstroem, Silkeborg, (DK)

Signed and Sealed this
Fourth Day of July, 2017

Joseph Matal
*Performing the Functions and Duties of the*
*Under Secretary of Commerce for Intellectual Property and*
*Director of the United States Patent and Trademark Office*